(12) United States Patent
Rebinsky et al.

(10) Patent No.: US 8,361,395 B2
(45) Date of Patent: Jan. 29, 2013

(54) LIGHT BASED FUEL SULFUR SENSOR AND SYSTEM

(75) Inventors: Douglas A. Rebinsky, Peoria, IL (US); Dong Fei, Peoria, IL (US); Svetlana M. Zemskova, Edelstein, IL (US)

(73) Assignee: Caterpillar Inc., Peoria, IL (US)

( * ) Notice: Subject to any disclaimer, the term of this patent is extended or adjusted under 35 U.S.C. 154(b) by 651 days.

(21) Appl. No.: 12/145,134

(22) Filed: Jun. 24, 2008

(65) Prior Publication Data
US 2009/0317299 A1    Dec. 24, 2009

(51) Int. Cl.
G01N 21/64 (2006.01)
G01N 21/66 (2006.01)
G01N 21/00 (2006.01)
G01N 15/06 (2006.01)
G01N 33/00 (2006.01)
G01N 33/48 (2006.01)

(52) U.S. Cl. .............. 422/82.08; 422/68.1; 422/82.05; 436/119

(58) Field of Classification Search .............. 422/52, 422/82.02, 82.08, 82.09; 436/123, 172
See application file for complete search history.

(56) References Cited

U.S. PATENT DOCUMENTS

| | | | |
|---|---|---|---|
| 3,795,812 A | 3/1974 | Okabe | |
| 4,077,774 A | 3/1978 | Neti et al. | |
| 4,272,486 A | 6/1981 | Harman, III | |
| 4,678,756 A | 7/1987 | Parks | |
| 5,152,963 A | 10/1992 | Wreyford | |
| 5,330,714 A | 7/1994 | Godec et al. | |
| 5,525,516 A | 6/1996 | Krutak et al. | |
| 5,545,897 A * | 8/1996 | Jack | 250/339.13 |
| 5,710,046 A | 1/1998 | Rutledge et al. | |
| 5,928,954 A | 7/1999 | Rutledge et al. | |
| 5,935,519 A | 8/1999 | Benner et al. | |
| 6,830,730 B2 | 12/2004 | Rhodes | |
| 2002/0026822 A1* | 3/2002 | Reading et al. | 73/31.05 |
| 2004/0168504 A1* | 9/2004 | Eden et al. | 73/23.2 |
| 2005/0074365 A1 | 4/2005 | Olstowski | |
| 2005/0260764 A1 | 11/2005 | Grigsby, Jr. et al. | |
| 2006/0258014 A1 | 11/2006 | Ceccarini et al. | |
| 2006/0263893 A1 | 11/2006 | Moses et al. | |
| 2007/0034551 A1 | 2/2007 | Lindstrom et al. | |

FOREIGN PATENT DOCUMENTS

| | | |
|---|---|---|
| JP | 56-133658 A | 10/1981 |
| JP | 01-302160 A | 12/1989 |

* cited by examiner

Primary Examiner — Sam P Siefke
Assistant Examiner — Bryan Kilpatrick
(74) Attorney, Agent, or Firm — Leydig, Voit & Mayer (57) ABSTRACT

An ultraviolet sensor arrangement detects the amount of sulfur in a fuel of an internal combustion engine by emitting an ultraviolet light field in the presence of the fuel. A detector is disposed to detect a responsive amount of fluorescent light and provide a sensing signal indicative of the amount of sulfur in the fuel. A filter (or filters) receives the sensing signal and provides a filtered sensing signal to a sensing circuit.

8 Claims, 5 Drawing Sheets

LIGHT BASED FUEL SULFUR SENSOR AND SYSTEM

TECHNICAL FIELD

This patent disclosure relates generally to fuel systems for internal combustion engines, and more particularly to systems and methods for sensing the fuel sulfur content within fuel systems.

BACKGROUND

Various initiatives and governmental regulations have been promulgated to address fuel efficiency and emission content of machines powered by internal combustion engines. Among other things, such regulations have required a reduction in the sulfur content in diesel and other fossil fuels used for internal combustion engines. For example, the Environmental Protection Agency of the United States established reduced sulfur requirements for diesel fuel for trucks, buses and other heavy-duty equipment that begin to take effect in 2007. Other government laws and regulations have created programs to improve the efficiency and/or emissions of older diesel engines. In these contexts, various requirements have thus limited the permitted sulfur content in diesel and other fossil fuels.

With the promulgation of these governmental regulations and standards, equipment manufacturers have developed engine components to operate within the guidelines. For example, the introduction of Ultra-low Sulfur Diesel (ULSD) fuel allows lower emissions, as do other renewable fuels and fuel products such as biodiesel and emulsifier additives. When these newer engine components are subjected to high levels of sulfur content in the fuel, they may be susceptible to undue wear and even failure over time. This is particularly true for the emission systems of such engines.

Accordingly, while various regulations have been implemented, there have been inadequate facilities for the detection of high sulfur content in fuels for internal combustion engines. This is particularly true in the case of vehicles used to transport goods such as highway trucks and the like.

BRIEF SUMMARY OF THE DISCLOSURE

The present disclosure relates to a sensor system and configuration for detecting an amount of sulfur in a fuel that is provided to an internal combustion engine. In an embodiment, an ultraviolet sensing arrangement for use with the fuel of an internal combustion engine includes an ultraviolet light source disposed to emit a known amount of light having a desired wavelength in the presence of the fossil fuel. A photo-sensitive detector, spaced from the light source, is disposed to detect the amount of fluorescent light present and to provide a sensing signal indicative of the amount of sulfur present in the fossil fuel. A filter may be used to receive the fluorescent light and to provide filtered fluorescent light, so that the effects caused by additives to the fuel may be at least partially removed. A sensing circuit is disposed to receive the sensing signal and to provide an output indicative of the amount of sulfur present in the fuel. The output may include either an alarm, or storing an event such as through data recording within an event data recorder for the machine.

In another aspect, the disclosure provides a method for detecting an amount of sulfur disposed in a fossil fuel for an internal combustion engine with the use of an ultraviolet light source, a photosensitive detector, and a sensing circuit. The method first illuminates the fossil fuel with light from the ultraviolet light source. Because the light emitted from the ultraviolet light source fluoresces in the presence of sulfur, the photo-sensitive detector detects the amount of fluorescent light present and provides a sensing signal indicative of the amount of sulfur present in the fossil fuel. A filter receives the sensing signal and provides a filtered sensing signal having signal effects provided by additives to the fossil fuel at least partially removed. The sensing circuit next receives the filtered sensing signal and provides an output indicative of the amount of sulfur present in the fuel.

DETAILED DESCRIPTION

The present disclosure relates to a method and sensing arrangement disposed to detect a level of sulfur content in fossil fuels. The sensing arrangement of the disclosure may be used in internal combustion engine powered machines such as transportation machines, constructions machines, and other machines. The disclosure also pertains to a method for detecting the amount of sulfur present in a fuel used in an internal combustion engine. The disclosed detection method includes a series of operations that can result in the logging of an event in a log or the like to record the detection of a fossil fuel with high sulfur content. In this way, a machine owner or operator may obtain a greater understanding of the operating conditions of the machine.

The disclosure has particular application in detecting sulfur content in fuels used for various types of machines, such as LSF and ULSF fuels. As used herein, the acronym "LSF" will denote Low Sulfur Fuel, while the term "ULSF" will denote Ultra-Low Sulfur Fuel, as those terms are understood by those skilled in the art.

Figure 1:
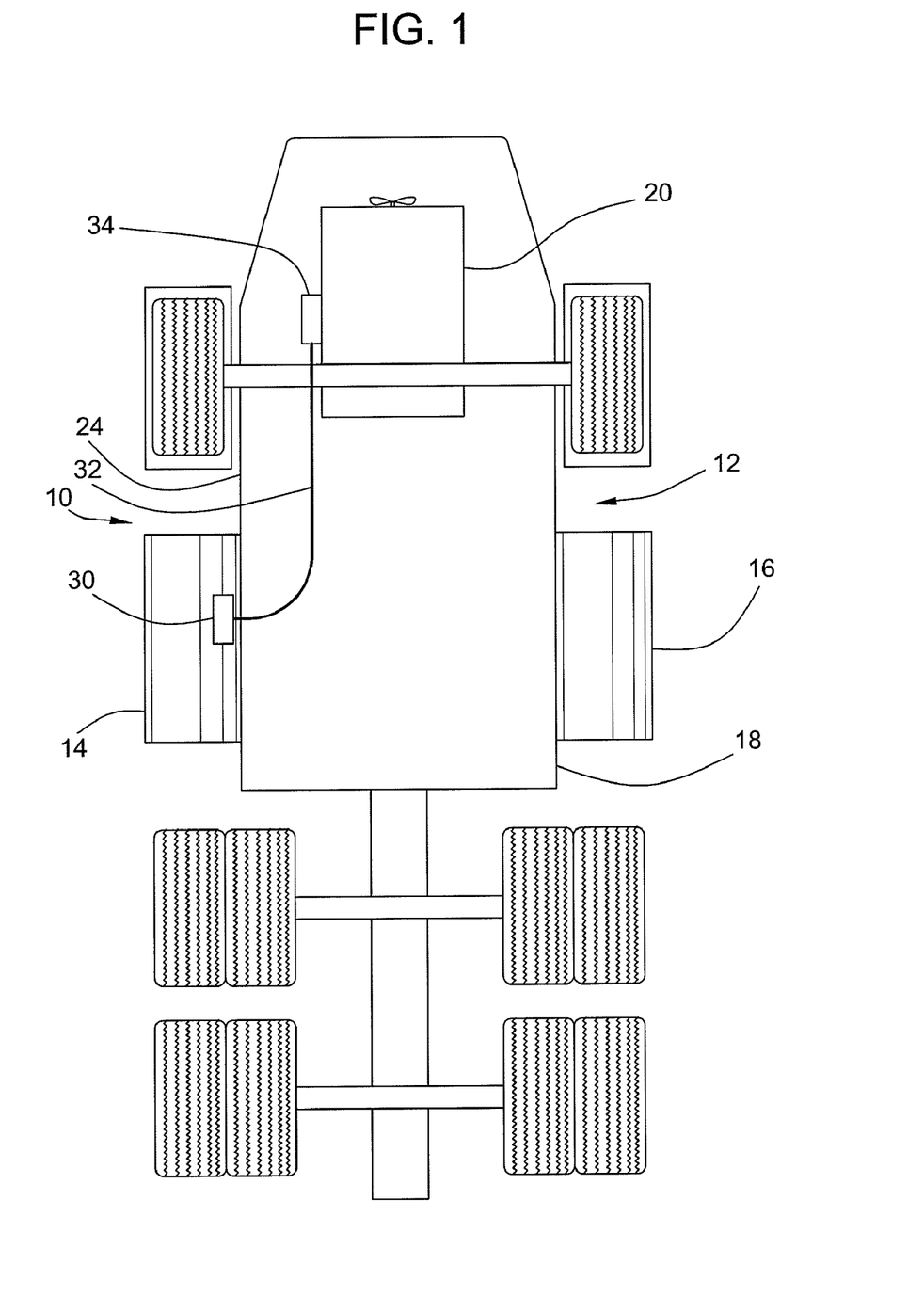
FIG. 1 is an outline view of a machine that uses a sulfur sensor arrangement according to the disclosure.

FIG. 1 is a simplified diagram illustrating an environment in which a sulfur detecting apparatus, as generally denoted by the numeral 10, may be employed. More specifically, a machine 12 such as an on-highway truck may include first and second fuel tanks 14, 16 which generally flank a machine chassis 18. In the illustrated embodiment, the first and second fuel tanks 14, 16 are disposed between intermediate front and rear tires of the machine 12. A fuel supply system (not shown) provides fuel from one or both of the first and second fuel tanks 14, 16 to an internal combustion engine 20, which is also supported by the chassis 18 as is known to those skilled in the art. This configuration is typical for on-highway trucks, but other configurations are also known.

A sensor arrangement 30, according to the disclosure, is disposed within the first fuel tank 14, such as by locating the sensing arrangement 30 on or close to the bottom of the first fuel tank 14 so that the sensor arrangement 30 is immersed within the fuel when the tank contains any appreciable amount of fuel. As explained in greater detail below, the sensor arrangement 30 generates a filtered sensing signal indicative of the amount of sulfur present within the fuel disposed in the first fuel tank 14. The sensor arrangement 30 is connected via a sensor connecting line 32 to an Electronic Control Module ("ECM") 34. In the illustrated embodiment, the ECM 34 is located within a compartment that houses the engine 20 and includes a microprocessor that operates in a logical fashion to help control engine functions. These functions are controlled with the use of sensors such as the sensor arrangement 30, which are disposed to monitor one or more engine parameters and diagnostic functions. While shown as located on or within the engine compartment, the ECM 34 could alternatively be located elsewhere, such as within an operator's cab (not shown) or the like.

In response to receipt of sensing signals provided by the sensor arrangement 30, the ECM 34 operates in logical fashion to provide indicia of the amount of sulfur in the fuel. For example, the ECM 34 may perform a set of instructions for generating and storing an event log that provides the date, time, and amount of detected sulfur in the fuel. Alternatively, or in addition to the creation of an event log, the ECM 34 may sound an alarm or otherwise notify the machine operator of the occurrence of an abnormal amount of sulfur in the fuel when the sulfur content exceeds a certain threshold.

Figure 2:
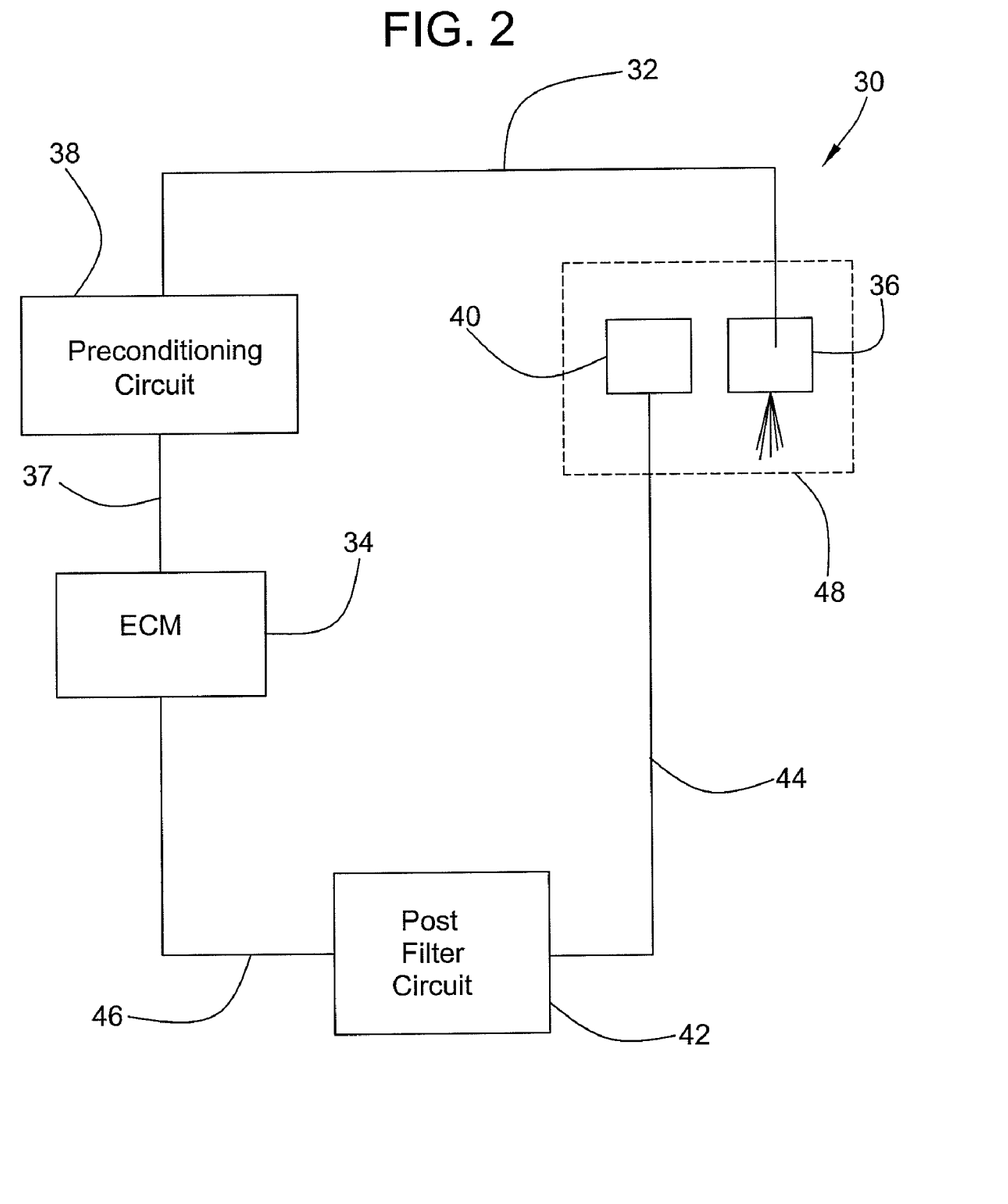
FIG. 2 is a simplified block diagram of a sulfur sensor arrangement according to an embodiment of the disclosure.

FIG. 2 illustrates a simplified block diagram of the sensor arrangement 30 and its connection with the ECM 34 and other components according to an embodiment of the disclosure. The sensor arrangement 30 includes an electro-luminescent light source, which in the illustrated embodiment is a light emitting diode (LED) 36. The LED 36 irradiates the fuel with light within a desired wavelength spectra, in this case in the ultraviolet wavelength range, upon the application of control signals from the ECM 34 via a line 37. In the illustrated embodiment, the ECM 34 provides control signals to a signal preconditioning circuit 38, as shown in FIG. 2. As explained below, the preconditioning circuit 38 may operate to provide conditioned control signals on the line 32 to the LED 36 for adjusting the wavelength output by the LED 36.

A photo-sensor 40, relatively closely spaced from the LED 36 (e.g., close enough to register emission from the fuel as stimulated by the LED), is disposed to detect the amount of visible light resulting from the irradiation of the fuel. The photo-sensor 40 thereafter passes a sensing signal in the form of a developed voltage or current signal to a post-filtering circuit 42 via a photo-sensor output line 44. A filtered sensing signal is thereafter provided to the ECM 34 via a filter output line 46 where it is further processed, as explained in greater detail below.

In order to provide sufficient photon energy to stimulate florescence of the sulfur in the fuel, the wavelength of light emitted by the electro-luminescent source is in the ultraviolet spectral range. In an embodiment, the LED 36 and the photo-sensor 40 are arranged within the same integrated package 48. The light emitted by the LED 36 is of a wavelength shorter than that of visible light, in the range of about 375 nanometers, which provides relatively high-energy photons. As the sulfur particles absorb the ultraviolet photons, internal energy promotions followed by emission-less decay occur. After a certain amount of emission-less decay, fluorescence in the visible range (e.g., about 425 to 550 nanometers) occurs and is detected by the photo-sensor 40.

In the absence of certain additives to the fuel, the intensity of the generated visible light generally varies in a linear fashion as a function of the amount of sulfur content in the fuel. In other words, as long as the number of UV photons greatly exceeds the number of available sulfur molecules, each additional sulfur molecule results in a proportional increase in the probability of fluorescence. Accordingly, the detected visible light intensity of a sample of fuel is used in an embodiment to determine the amount of sulfur present in the fuel.

Figure 3:
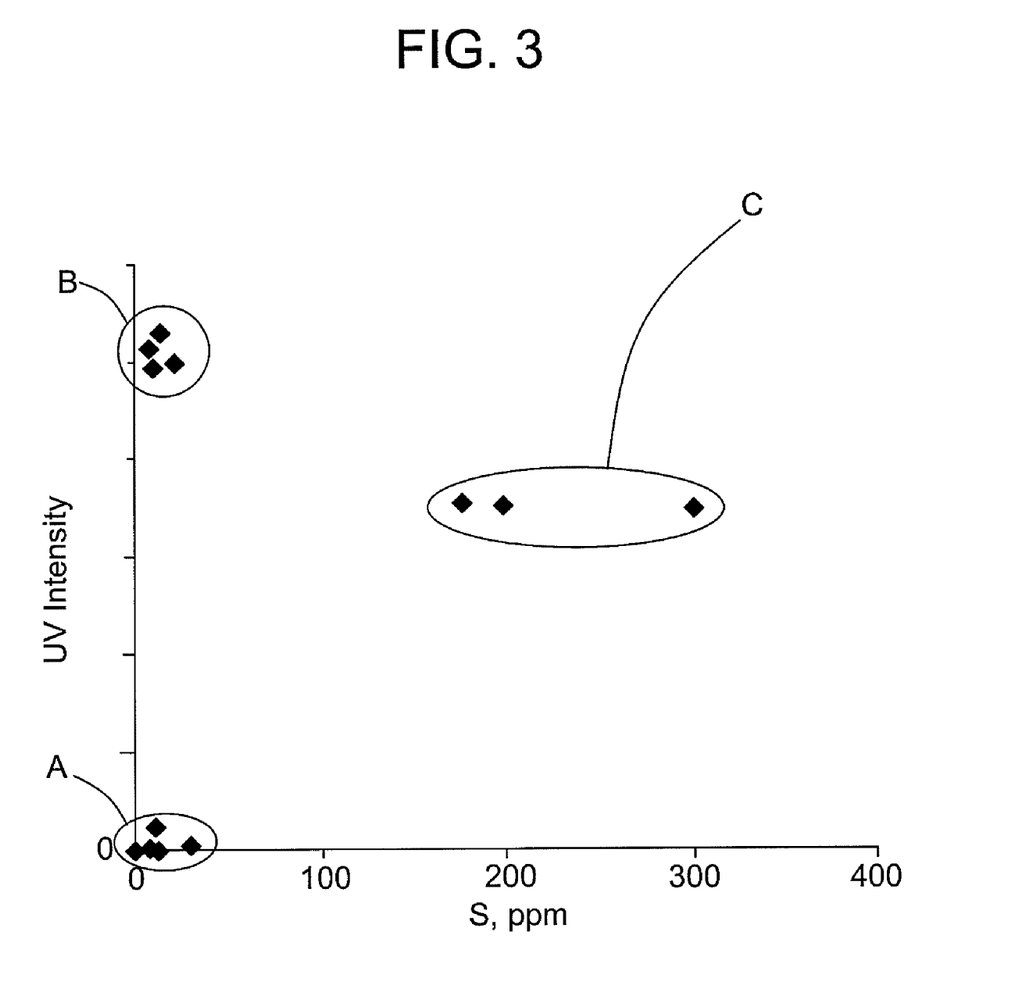
FIG. 3 is a graphical representation illustrating detection of various amounts of sulfur in certain types of fuels prior to the application of filtering according to an embodiment of the disclosure.

It has been found, however, that certain particles present in fuels of conventional types may also contribute to the intensity of detected visible light. For example, certain types of ULSF contain additives that contribute to detected light intensity. In these circumstances, the fluorescence intensity output can be misleading since it is not indicative of sulfur content only. FIG. 3 illustrates various fuel samples exposed to UV light in the absence of the application of any pre-filtering or post-filtering steps which are explained below. A first sample of ULSF, denoted by the letter A provides a detected output intensity level within an expected range, when considering only the contribution of sulfur within the fuel. That is, the amount of sulfur in this sample is significantly less than 100 ppm. A second sample of ULSF denoted by the letter B, however, may yield a greater detected light intensity even though the contribution of sulfur is approximately the same as in the case of sample A, in this case also significantly less than 100 ppm. The increased detected intensity may be due to the contribution in the sample of additives within the ULSF that provide a fluorescence response in the presence of UV light that is similar to, though not identical to, that of sulfur particles. By way of comparison, a sample of LSF, denoted by the letter C in FIG. 3, provides an intensity level that is similar to the intensity level of sample B even though the amount of sulfur in the sample is on the order of 200 ppm, far greater than the amount of sulfur in sample B.

Further principles disclosed herein can be used with various fuel types to differentiate the contribution of sulfur to the detected output. In an embodiment, to discriminate between sulfur species and other species having different coefficients of UV light absorption or fluorescence, the detected signal is passed through a filter, such as the post-filtering circuit 42 shown in FIG. 2. The post-filtering circuit operates to at least attenuate the contribution of, and may remove, spectral or output signatures that differ from that of sulfur particles. In this way, the contribution of non-sulfur particles attenuated. Alternatively, the post-filtering circuit 42 may provide correction factors to the detected signal based upon an analysis of the spectral signatures provided in the detected signal. Therefore, the post-filtering circuit 42 shown in FIG. 2 may be implemented as one or more filtering circuits disposed to differentiate sulfur and other contributions among various fuel types, such as a first filter circuit for filtering chemical species of a one coefficient of light absorption and a second filter circuit for detecting other chemical species of another coefficient of light absorption.

Figure 4:
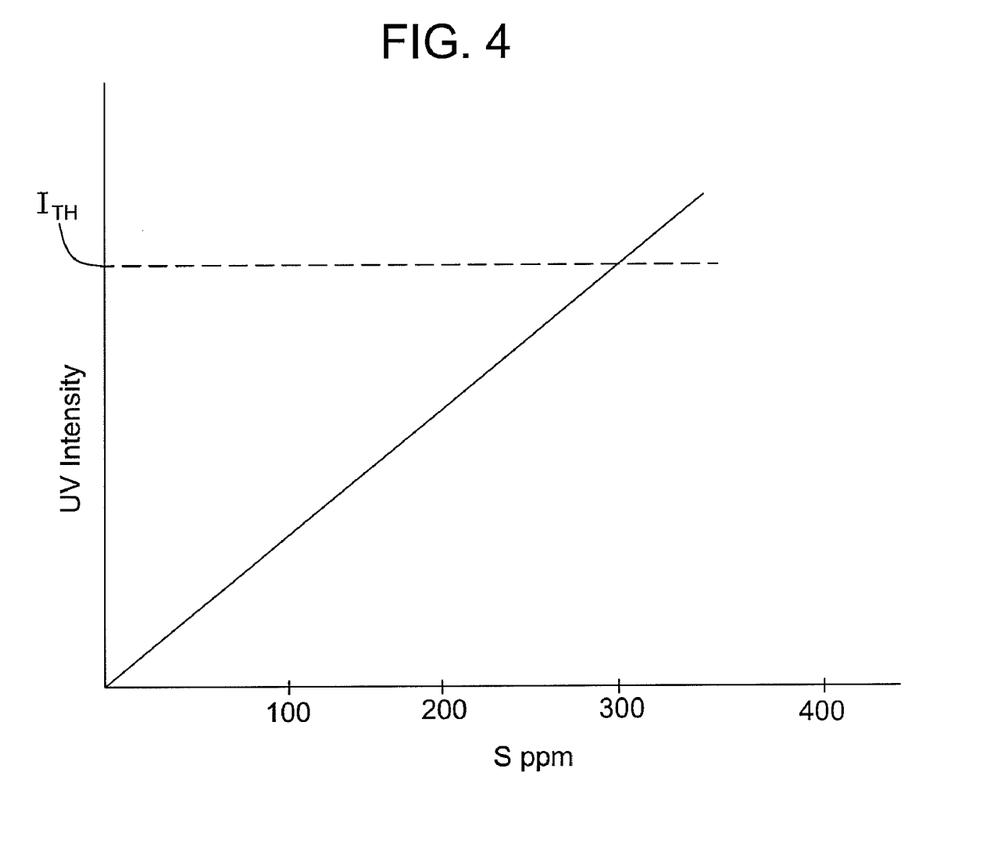
FIG. 4 is a graphical representation illustrating the relationship between the amount of sulfur detected in fuels and the output illumination detected by the sensing arrangement.

FIG. 4 illustrates an idealized illumination intensity output that varies as a function of amount of sulfur species disposed in various fuel samples. As shown, with the application of either pre-filtering of the illumination source, post-filtering of the detected light intensity or both, the generated sensing signal corresponding to the illumination output is generally linear, as shown in FIG. 4. FIG. 4 further illustrates an illumination threshold $I_{TH}$ that represents a maximum intensity level and a corresponding maximum sulfur species level in the fuel. Upon detection of an illumination that exceeds the illumination threshold $I_{TH}$, the arrangement may be programmed to cause an alarm to be activated or to take corrective action. In addition, the arrangement may be programmed to store an event log, as explained in further detail below.

Upon receipt of a filtered detection signal by the ECM 34, the amount of sulfur present in the fuel may be determined according to various methodologies. For example, an embodiment of the disclosure utilizes a look-up table that correlates a detected signal level with the amount of sulfur present therein. That is, the ECM 34 may perform a look-up of data values that correlate the obtained data set with data sets for known fuels. In this way, the disclosure may discriminate between different types of ULSF, LSF and other fuels based on known additives of various fuel suppliers. Alternatively, the system may retrieve an appropriate scale factor, based on the retrieved data, and apply the scale factor to the detected intensity value to calculate an amount of sulfur content in the fuel sample.

In an embodiment, the above-noted sulfur content detection steps occur upon the initiation of a fueling operation. In this example, the sulfur detection steps may be performed within a determined period after the operator has removed a fuel cap. However, the system may alternatively be programmed to perform the steps above on a periodic basis, or upon the occurrence of another event.

Figure 5:
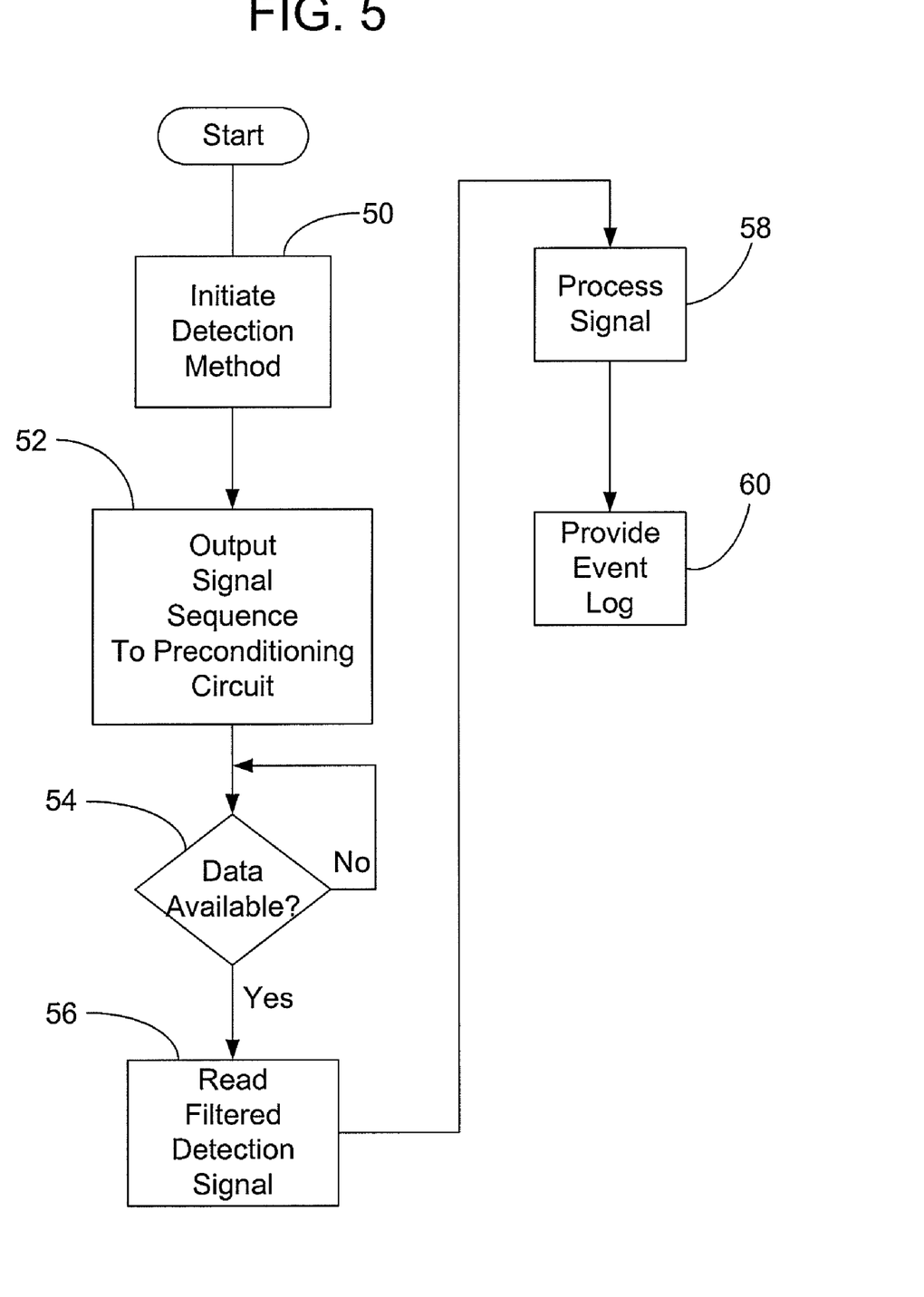
FIG. 5 is a flow diagram of the logical steps taken by an Electrical Control Module (ECM) in the embodiment illustrated in FIG. 2.

FIG. 5 illustrates the manner in which various steps that may be performed according to an embodiment of the disclosure. It will be appreciated that the noted steps and other steps performed by the ECU and other electronic logical components are executed by the execution of computer-readable instructions stored on a computer-readable medium such as a disk, chip, RAM, ROM, etc. The illustrated steps may be performed by the ECM 34, which initiates the process at a first stage 50 based on a detected removal of a fuel cap or similar action indicating that the operator is filling a fuel tank. Alternatively, the ECM 34 may perform the method at periodic intervals. After initiation, the method proceeds to a next stage 52 and provides output signals to the preconditioning circuit 38. This enables the detection apparatus to provide irradiation of light within either a relatively narrow wavelength range, or alternatively to provide multiple wavelengths for discriminating among various chemical species of interest.

The method then proceeds to a decision stage 54 and determines whether data is available from the detection apparatus. For example, the ECM 34 may poll the filter output line 46 to determine whether new data has been supplied from the filter or filters of the detection apparatus. If data is available, the ECM 34 reads the data corresponding to the filtered detection signal at a reading stage 56. The ECM 34 may then process the data corresponding to the filtered detection signal at a processing stage 58. For example, the ECM 34 may access a look-up table to determine an amount corresponding to the amount of sulfur present in the fuel sample.

INDUSTRIAL APPLICABILITY

The industrial applicability of the process and detection apparatus used to monitor the sulfur content in a fossil fuel for powering a machine will be readily appreciated from the foregoing discussion. As described, a detection device apparatus based on application of ultraviolet light to the fuel and detecting the amount of light based on the energy absorbed by the fuel provides an output signal with an intensity corresponding to the amount of sulfur in the fuel. Data corresponding to one or more such output signals may be recorded in one or more event logs, identifying the date and time of a data recording. Alternatively, the detection apparatus may be used to signal an alarm or warning light to the machine operator to indicate that fuel with an abnormally high sulfur level is being utilized. Accordingly, the disclosure may be used to monitor the sulfur content in fuels provided to an internal combustion engine.

The present disclosure is applicable to monitor the sulfur content for the fuel in a machine such as an on-highway track that is capable of multiple fuelings with varying types of fuel over time. Advantageously, the present disclosure provides a relatively low cost data gathering apparatus and method that avoids data scattering for various types of fuels, such as ULSF provided by different fuel suppliers. Because emission aftertreatment system components tend to malfunction or deteriorate over time in the presence of fuel with excessive sulfur content, the disclosure is particularly useful in avoiding such conditions. In addition, it is relatively simple to install and to maintain. The disclosure may thus be employed in new machines equipped with components that are intended for use with low-sulfur fuels. There are also a number of older models of such machines in circulation, and the ability to retrofit or rework them to include the present disclosure is advantageous and cost-effective. As can be appreciated, the detection process described herein may be carried out by the use of many alternative procedures or operations.

Accordingly, it will be appreciated that the foregoing description provides examples of the disclosed system and technique. However, it is contemplated that other implementations of the disclosed principles will differ in detail from the foregoing examples. All discussions of specific examples are intended to reference the particular example being discussed at that point and are not intended to imply any limitation as to the scope of the present disclosure more generally. All language of distinction and disparagement with respect to certain features is intended to indicate a lack of preference for those features, but not to exclude such from the scope of the disclosed principles entirely unless otherwise indicated.

All methods described herein can be performed in any suitable order unless otherwise indicated herein or otherwise clearly contradicted by context. Accordingly, the disclosed innovations includes all modifications and equivalents of the subject matter recited in the claims appended hereto as permitted by applicable law. Moreover, any combination of the above-described elements in all possible variations thereof is encompassed unless otherwise indicated herein or otherwise clearly contradicted by context.

We claim:

1. A method of using a detection apparatus for detecting an amount of sulfur content in a sample of liquid fossil fuel including sulfur particles having a first coefficient of light absorption provided to an internal combustion engine disposed to power a machine, the detection apparatus including a light source, a light-sensitive detector disposed proximate the light source, a filter circuit electrically connected to the light-sensitive detector and an electronic control module in communication with the filter circuit, the method comprising:
    irradiating at least a portion of the liquid fossil fuel sample in a fuel tank of the machine with the light source having a desired wavelength spectra to cause sulfur particles in the liquid fossil fuel sample to emit an illumination;
    detecting the intensity of the illumination with the light-sensitive detector and providing, by the light-sensitive detector, a detection signal indicative of the detected intensity of the illumination to the filter circuit;
    filtering the detection signal with the filter circuit, the filter circuit adapted to differentiate a contribution to the detected intensity of the illumination caused by a non-sulfur particle in the liquid fossil fuel sample, and providing a filtered detection signal indicative of the detected intensity of the illumination less any contribution to the detected intensity of the illumination caused by said non-sulfur particle in the liquid fossil fuel sample;

processing the filtered detection signal with the electronic control module and providing an output indicative of the amount of sulfur particles in the liquid fossil fuel based upon the filtered detection signal.

2. The method of claim 1 further comprising the step of:
storing an event log by the electronic control module relating to the output, the event log providing indicia of the date and time in which the output was obtained.

3. The method of claim 1 wherein the desired spectra is in the ultraviolet range.

4. The method of claim 3, wherein the step of irradiating further comprises preconditioning the light source by apply varying wavelengths to the liquid fossil fuel sample.

5. The method of claim 1 wherein the step of filtering the detection signal includes applying a filter to attenuate the intensity of the detection signal caused by non-sulfur chemical species having a second coefficient of light absorption.

6. The method of claim 4 wherein the step of filtering the detection signal includes applying a filter to attenuate the intensity of the detection signal caused by non-sulfur particles having a second coefficient of light absorption.

7. The method of claim 1 further including the step of performing a table look-up by the electronic control module to determine an amount of sulfur content in the fuel.

8. The method of claim 7 further including the step of providing a visual output to an operator of the machine when the amount of sulfur content in the liquid fossil fuel sample exceeds a threshold.

* * * * *

UNITED STATES PATENT AND TRADEMARK OFFICE
CERTIFICATE OF CORRECTION

| | | |
|---|---|---|
| PATENT NO. | : 8,361,395 B2 | Page 1 of 1 |
| APPLICATION NO. | : 12/145134 | |
| DATED | : January 29, 2013 | |
| INVENTOR(S) | : Rebinsky et al. | |

It is certified that error appears in the above-identified patent and that said Letters Patent is hereby corrected as shown below:

In the Specification

Column 6, line 5, delete "on-highway track" and insert -- on-highway truck --.

Signed and Sealed this
Eleventh Day of August, 2015

Michelle K. Lee
*Director of the United States Patent and Trademark Office*